United States Patent

Suh et al.

[11] Patent Number: 5,913,872
[45] Date of Patent: Jun. 22, 1999

[54] MAGNETIC NOSE CLIP

[75] Inventors: David H. Suh, Elkins Park, Pa.; Bo Kook Choi, Seoul, Rep. of Korea

[73] Assignee: Newcore, USA, Philadelphia, Pa.

[21] Appl. No.: 08/948,172

[22] Filed: Oct. 10, 1997

[51] Int. Cl.[6] .................................................. A61B 17/00
[52] U.S. Cl. ......................... 606/201; 606/204; 606/191; 606/199; 606/204.45
[58] Field of Search .................................... 606/198, 199, 606/204.15, 204.45, 201; D24/135

[56] References Cited

U.S. PATENT DOCUMENTS

| | | | |
|---|---|---|---|
| D. 375,552 | 11/1996 | Davi | D24/106 |
| 4,033,342 | 7/1977 | Lake | 128/140 N |
| 4,369,783 | 1/1983 | Hiller et al. | 128/260 |
| 4,445,508 | 5/1984 | Lake | 128/201.18 |
| 4,457,756 | 7/1984 | Kern et al. | 604/286 |
| 4,759,365 | 7/1988 | Askinazy | 128/342 |
| 5,185,005 | 2/1993 | Ballantyne | 604/174 |

*Primary Examiner*—Michael Buiz
*Assistant Examiner*—Vy Quang Bui
*Attorney, Agent, or Firm*—Klehr, Harrison, Harvey, Branzburg & Ellers, LLP

[57] ABSTRACT

A device for applying a continuous pressure and magnetic field to the septum of a wearer. The device comprises a generally U-shaped member comprising a base and two parallel arms, each of said arms being inserted into a nostril of a wearer, said arms being further biased toward said septum; canted bulbous protrusions at the ends of said legs for applying pressure to the septum of the wearer; and magnets within the bulbous protrusions for facilitating the closure of said arms and legs and for applying a magnetic field to said septum.

11 Claims, 1 Drawing Sheet

MAGNETIC NOSE CLIP

FIELD OF THE INVENTION

The present invention is directed to nasal clips. In particular, the present invention is directed to nasal clips which apply a constant pressure on the septum of the wearer, thereby providing therapeutic results.

BACKGROUND OF THE INVENTION

The present invention is directed to nasal clips which apply pressure on the septum of the wearer. Prior art nasal clip devices have typically served a number of purposes. First, they have been utilized to keep the nasal passages of the wearer open while the wearer is asleep. Secondly, these clips have been used to control snoring. Thirdly, they have been used to block the nasal passages in athletes and most particularly for swimmers. Finally, nasal clips have been utilized for first aid and medical applications such as for controlling nose bleeds and for supporting devices such as anesthetic face masks.

There are a number of prior art patents which disclose nasal clip embodiments. U.S. Design Pat. No. 375,552 discloses an improved nasal clip comprising a horseshoe shaped member which applies pressure on the septum of a wearer. U.S. Pat. No. 4,369,783 discloses a nose clip for the prophylactic or therapeutic treatment of cattle. The clip comprises a bow whose ends are designed to receive active ingredients in the form of medicines. The receiving ends are inclined towards each other to hold the clip in place within the animal's nose.

U.S. Pat. No. 4,457,756 discloses a clip for treatment of nose bleeds having opposed legs which apply constant pressure on the nasal mucosa lying on the septum immediately inside the nostrils. This patent discloses a number of embodiments for clips which apply continuous pressure to the septum of a wearer.

U.S. Pat. No. 4,759,365 discloses a spring-coil wire device comprising a pair of barrel-shaped bodies constructed of a resilient material and including a plurality of peripherally spaced and generally U-shaped body segments which apply a constant pressure on the nasal passages and nasal septum of the wearer.

Finally, U.S. Pat. Nos. 4,445,508 and 4,033,342 disclose nasal clips which fit on the outside of the nose of the wearer and which apply constant pressure on the nasal passages. These clips are mainly utilized for swimmers.

While there are a number of prior art devices which provide nasal opening and septum pressure systems, none of these devices include a magnetic closure system. It would be desirable to provide a nasal clip which applies a constant pressure to the septum of a wearer including the use of magnets to draw the clips together and hold them against the nasal septum. The use of magnets would provide constant pressure on the septum and would apply a therapeutic magnetic field. Such a clip would minimize snoring and open the nasal passages by stimulating the nerves of the septum. These and other objects of the present invention are set forth in the following detailed description and the claims which follow.

SUMMARY OF THE INVENTION

In accordance with the present invention, a device for applying a continuous pressure to the septum of a wearer is disclosed. The device comprises a generally U-shaped member comprising a base and two generally parallel legs for insertion into the nose of a wearer and for surrounding the septum, each of said generally parallel legs extending into a nostril of the wearer; and a magnet within each of said legs for drawing the legs toward the nasal septum of the wearer and for applying a magnetic field to the septum of the wearer.

In a more preferred embodiment, a device for applying a continuous pressure and magnetic field to the septum of a wearer is disclosed. The device comprises a generally U-shaped member having a base and two parallel arms, each said arm being inserted into a nostril of a wearer, said legs being further biased toward said septum; bulbous protrusions at the ends of said legs for applying pressure to the septum of the wearer; and magnets within the bulbous protrusions for facilitating the closure of said legs and for applying a magnetic field to said septum.

In still another embodiment, the present invention comprises a device for applying a continuous pressure and magnetic field to the septum of a wearer comprising; a generally U-shaped member comprising a base and two parallel legs, each of said arms being inserted into a nostril of a wearer, said legs being further biased toward said septum; canted bulbous protrusions at the ends of said legs for applying pressure to the septum of the wearer; and magnets within the bulbous protrusions for facilitating the closure of said legs and for applying a magnetic field to said septum. These and other objects of the present invention will be discussed in further detail below.

DETAILED DESCRIPTION OF THE PRESENT INVENTION

Figure 1:
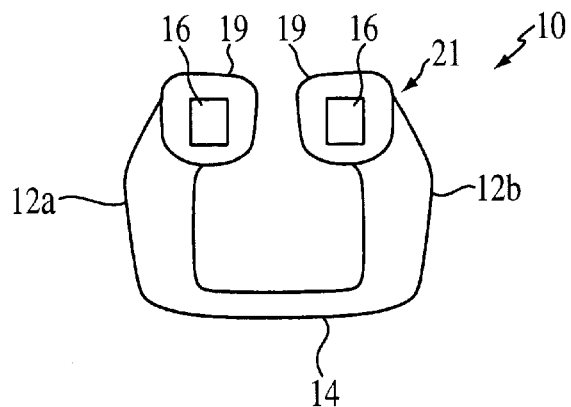
FIG. 1 is an elevational view of the nose clip of the present invention.
Figure 2:
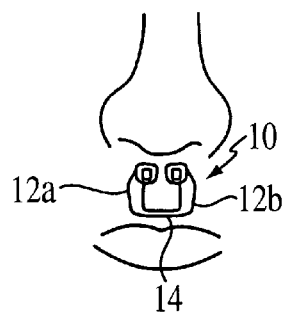
FIG. 2 is a perspective view of the nose clip of the present invention prior to its insertion into the nose of a wearer.
Figure 3:
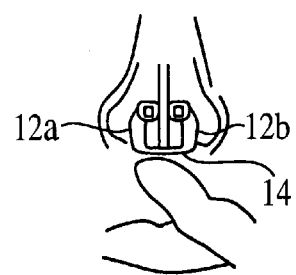
FIG. 3 is a perspective view of the nose clip of the present invention being inserted into the nose of a wearer.
Figure 4:
FIG. 4 is a side perspective view of the nose clip in the wearer.
Figure 5:
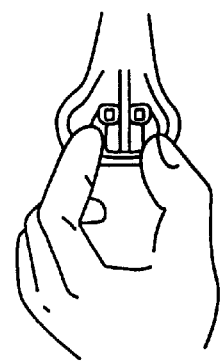
FIG. 5 is a section view of the nose clip of the present invention being adjusted within the nose of a wearer.

The present invention is now described with reference to the enclosed figures wherein the same numbers are utilized where applicable. Referring to FIG. 1, the present invention comprises in one embodiment, a U-shaped nasal clip 10. Preferably, the clip 10 is constructed from a suitable polymeric material or plastic such as polyamide, polystyrene, polypropylene, and polyacetal (polyoxymethylene). The thickness of the clip may vary within limits depending upon the materials used.

The U-shaped clip 10 comprises two parallel legs 12a, 12b separated by a base leg 14. The U-shaped clip 10 fits within the nose of the wearer and legs 12a, 12b surround the septum of the wearer. Each leg 12a, 12b extends into a nostril of the wearer. The legs 12a, 12b of the U-shaped member are biased inward and the ends are incanted 21 to apply a constant pressure against the septum when the clip 10 is inserted into the nose of the wearer.

A key and critical feature of the present invention is the inclusion of magnets 16 within the ends of the legs 12a, 12b. The magnets apply a constant pressure against the septum and generate a magnetic field which produces therapeutic results. As shown, the magnets 16 are retained in bulbous protrusions 19 at the ends of the legs 12a, 12b. The bulbous protrusions 19 are canted inwardly 21 toward the septum of the wearer.

The application of the present invention is most particularly shown with respect to FIGS. 2 through 5. As shown, the clip 10 of the present invention is inserted into the nose, whereby each leg 12a, 12b enters a nostril 18 of the wearer and surrounds the septum 20. The bottom of the septum of the nose then abuts against the base 14 of the clip. As shown most particularly in FIG. 5, the clip is then adjusted for the comfort and convenience of the wearer.

The magnets 16 contained within the bulbous protrusions 19 apply constant magnetic pressure which keeps the clips secure against the wearer. The magnets further apply a magnetic field which may stimulate the septum of the wearer. The clip 10 eliminates snoring and opens breathing passages. The present invention may also be worn during exercise.

It is to be appreciated that other embodiments fulfill the scope of the present invention and that the true nature of the scope of the present invention is to be determined with reference to the claims appended hereto.

We claim:

1. A device for applying a continuous pressure to the septum of a wearer, comprising:

a generally U-shaped polymeric member comprising a base and two generally parallel legs for insertion into the nose of the wearer and for surrounding the septum, each of said generally parallel legs extending into a nostril of the wearer;

a magnet within each of said legs for drawing the legs toward the nasal septum of the wearer and for applying a magnetic field to the septum of the wearer.

2. The device of claim 1 wherein said polymeric material comprises polyamide.

3. The device of claim 1 wherein said polymeric material comprises polystyrene.

4. The device of claim 1 wherein said polymeric material comprises polypropylene.

5. The device of claim 1 wherein said polymeric material comprises polyacetal.

6. A device for applying a continuous pressure and magnetic field to the septum of a wearer comprising:

a generally U-shaped polymeric member having a base and two parallel legs, each said legs being inserted into a nostril of a legs, said legs being further biased toward said septum;

bulbous protrusions at the ends of said legs for applying pressure to the septum of the wearer; and magnets within the bulbous protrusions for facilitating the closure of said legs and for applying a magnetic field to said septum.

7. The device of claim 7 wherein said polymeric material comprises polyamide.

8. The device of claim 7 wherein said polymeric material comprises polystyrene.

9. The device of claim 7 wherein said polymeric material comprises polypropylene.

10. The device of claim 7 wherein said polymeric material comprises polyacetal.

11. A device for applying a continuous pressure and magnetic field to the septum of a wearer comprising:

a generally U-shaped polymeric member comprising a base and two parallel legs, each of said legs being inserted into a nostril of a wearer, said legs being further biased toward said septum;

canted bulbous protrusions at the ends of said legs for applying pressure to the septum of the wearer; and magnets within the bulbous protrusions for facilitating the closure of said legs and for applying a magnetic field to said septum.

* * * * *